(12) United States Patent
Vija et al.

(10) Patent No.: US 11,647,973 B2
(45) Date of Patent: May 16, 2023

(54) THREE-DIMENSIONAL TILEABLE GAMMA RAY DETECTOR

(71) Applicant: Siemens Medical Solutions USA, Inc., Malvern, PA (US)

(72) Inventors: Alexander Hans Vija, Evanston, IL (US); Miesher Rodrigues, Buffalo Grove, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 204 days.

(21) Appl. No.: 17/302,464

(22) Filed: May 4, 2021

(65) Prior Publication Data
US 2022/0354443 A1    Nov. 10, 2022

(51) Int. Cl.
*A61B 6/00* (2006.01)
*G01T 1/17* (2006.01)

(52) U.S. Cl.
CPC .......... *A61B 6/4258* (2013.01); *A61B 6/4411* (2013.01); *A61B 6/4452* (2013.01); *A61B 6/4488* (2013.01); *G01T 1/17* (2013.01)

(58) Field of Classification Search
CPC ....................................................... G01T 1/17
See application file for complete search history.

(56) References Cited

U.S. PATENT DOCUMENTS

| | | | | |
|---|---|---|---|---|
| 5,742,060 A | * | 4/1998 | Ashburn | G01T 1/2018 |
| | | | | 250/370.09 |
| 5,821,541 A | * | 10/1998 | Turner | G01T 1/2928 |
| | | | | 250/363.03 |
| 5,943,388 A | * | 8/1999 | Turner | G01V 5/0041 |
| | | | | 378/98.9 |
| 6,175,611 B1 | * | 1/2001 | Melen | G01T 1/243 |
| | | | | 378/98.2 |
| 6,194,726 B1 | * | 2/2001 | Pi | G01T 1/161 |
| | | | | 250/363.02 |
| 6,323,492 B1 | | 11/2001 | Clinthorne | |
| 9,606,245 B1 | * | 3/2017 | Czarnecki | G01T 1/208 |
| 2003/0205675 A1 | * | 11/2003 | Nelson | G01T 1/2928 |
| | | | | 250/370.09 |
| 2003/0205676 A1 | * | 11/2003 | Nelson | A61B 6/4258 |
| | | | | 250/370.09 |
| 2003/0209662 A1 | * | 11/2003 | Nelson | G01T 1/244 |
| | | | | 250/252.1 |

(Continued)

FOREIGN PATENT DOCUMENTS

| | | |
|---|---|---|
| EP | 1119290 B1 | 11/2008 |
| WO | 2020032921 A1 | 2/2020 |

(Continued)

*Primary Examiner* — Blake C Riddick

(57) ABSTRACT

For gamma ray detection, 3D tiling is made possible by modules that include a gamma ray detector with at least some electronics extending away from the detector as a side wall, leaving an air or low attenuation gap behind the gamma ray detector. The modules may be stacked to form arrays of any shape in 3D, including stacking to form a Compton detector with a scatter detector separated from the catcher detector by the low attenuation gap where the electronics form at least one side wall between the detectors. The modules may be stacked so that the detectors from the different modules are in different planes and/or not part of a same surface (e.g., same surface provided with just 1D or 2D tiling).

21 Claims, 5 Drawing Sheets

(56) References Cited

U.S. PATENT DOCUMENTS

| | | | | |
|---|---|---|---|---|
| 2004/0004189 | A1* | 1/2004 | Brahme | G01T 1/24 250/370.08 |
| 2004/0021083 | A1* | 2/2004 | Nelson | G01T 1/249 250/252.1 |
| 2004/0195512 | A1* | 10/2004 | Crosetto | A61B 6/037 250/363.04 |
| 2004/0251419 | A1* | 12/2004 | Nelson | G01T 1/243 250/370.09 |
| 2005/0253073 | A1* | 11/2005 | Joram | G01T 1/2985 250/366 |
| 2007/0040126 | A1* | 2/2007 | El-Hanany | G01T 1/202 250/370.1 |
| 2007/0096031 | A1* | 5/2007 | Meier | G01T 1/1644 250/370.11 |
| 2008/0156993 | A1 | 7/2008 | Weinberg et al. | |
| 2008/0217552 | A1* | 9/2008 | Tumer | A61B 6/4258 327/306 |
| 2009/0290680 | A1* | 11/2009 | Tumer | G01T 1/247 250/311 |
| 2010/0025592 | A1* | 2/2010 | Tumer | G01T 1/2928 250/371 |
| 2010/0096555 | A1* | 4/2010 | Nelson | G01T 1/2002 250/361 R |
| 2010/0204942 | A1* | 8/2010 | Danielsson | G01T 1/243 702/85 |
| 2011/0192983 | A1 | 8/2011 | Yu et al. | |
| 2011/0240864 | A1* | 10/2011 | Degenhardt | G01T 1/1644 250/362 |
| 2011/0253901 | A1* | 10/2011 | Chmeissani Raad | G01T 1/249 250/370.09 |
| 2011/0286576 | A1* | 11/2011 | Cui | A61B 6/4291 378/62 |
| 2012/0161019 | A1 | 6/2012 | Tsuji et al. | |
| 2013/0026380 | A1* | 1/2013 | Tkaczyk | G01T 1/2928 438/73 |
| 2014/0183369 | A1* | 7/2014 | Frisch | G01T 1/2928 250/366 |
| 2014/0307850 | A1 | 10/2014 | Poorter et al. | |
| 2014/0312238 | A1* | 10/2014 | Liu | G01T 1/1618 250/366 |
| 2015/0092913 | A1* | 4/2015 | Hu | A61B 6/56 378/19 |
| 2015/0323685 | A1* | 11/2015 | Nelson | G01T 1/242 250/370.08 |
| 2015/0331115 | A1* | 11/2015 | Nelson | G01T 1/1612 250/366 |
| 2017/0285191 | A1 | 10/2017 | Hugg et al. | |
| 2018/0136340 | A1* | 5/2018 | Nelson | G01T 1/1611 |
| 2018/0172847 | A1* | 6/2018 | Nelson | A61B 6/037 |
| 2019/0187302 | A1* | 6/2019 | Nelson | G01T 1/2018 |
| 2019/0282185 | A1* | 9/2019 | Gregerson | A61B 6/4488 |
| 2019/0339402 | A1* | 11/2019 | Crestani | G01T 1/243 |
| 2019/0353807 | A1* | 11/2019 | Furenlid | G01T 1/2985 |
| 2019/0383955 | A1* | 12/2019 | Hjärn | G01T 1/243 |
| 2020/0096656 | A1* | 3/2020 | Nelson | G01T 1/247 |
| 2020/0158896 | A1* | 5/2020 | Danielsson | G01T 1/242 |
| 2021/0285897 | A1* | 9/2021 | Read | G01N 23/046 |
| 2022/0167936 | A1* | 6/2022 | Sundberg | A61B 6/486 |
| 2022/0211334 | A1* | 7/2022 | Furenlid | G01T 1/202 |

FOREIGN PATENT DOCUMENTS

| | | |
|---|---|---|
| WO | 2020032922 A1 | 2/2020 |
| WO | 2020032923 A1 | 2/2020 |

* cited by examiner

THREE-DIMENSIONAL TILEABLE GAMMA RAY DETECTOR

BACKGROUND

The present embodiments relate to gamma ray detectors, such as for nuclear medical imaging. A detector is positioned to detect emitted gamma rays.

One or two-dimensional (1D or 2D) tillable gamma-ray detectors are used in many applications, such as deep space exploration, homeland security, nuclear medicine, nuclear power plants, and nuclear processing facilities. The electronics, heat sink, EMI shielding, and other components are implemented in layers beneath the active detection area, partially or completely blocking photons and photon scattering from one layer into other layers beneath. This type of implementation is not ideal for multi-scattering layers of active detection materials with optimal signal-to-noise performance. Compton imaging relies on scatter and catcher detectors, so is particularly susceptible to attenuation caused by components behind one of the detectors. Electronics may be positioned outside a footprint of the detectors, which reduces the ability to tile detectors in 1D or 2D and may degrade signal-to-noise.

SUMMARY

By way of introduction, the preferred embodiments described below include methods and systems for gamma ray detection. 3D tiling is made possible by modules that include a gamma ray detector with at least some electronics extending away from the detector as a side wall, leaving an air or low attenuation gap behind the gamma ray detector. The modules may be stacked to form arrays of any shape in 3D, including stacking to form a Compton detector with a scatter detector separated from the catcher detector by the low attenuation gap where the electronics form at least one side wall between the detectors. The modules may be stacked so that the detectors from the different modules are in different planes and/or not part of a same surface (e.g., same surface provided with just 1D or 2D tiling).

In a first aspect, a gamma ray detector system is provided for medical imaging. A gamma ray detector includes a plate having first and second parallel, largest surfaces. At least one circuit board has an edge between first and second parallel, largest surfaces. The edge is positioned adjacent to the first surface of the gamma ray detector such that the first surface of the circuit board is at an angle between 45 degrees and 135 degrees (e.g., about 90 degrees or orthogonal) from the first surface of the gamma ray detector. A gap has gas (e.g., air) and is formed between the at least one circuit board and the gamma ray detector due to the positioning of the at least one circuit board at the angle to the first surface of the gamma ray detector. The gap has a gap volume at least ten times a gamma ray detector volume of the gamma ray detector.

In one embodiment, two circuit boards are positioned parallel to each other at the angle to the first surface of the gamma ray detector. The edges of the two circuit boards are positioned within 10% of a length of the first surface of the gamma ray detector to opposite edges of the first surface of the gamma ray detector such that the gap is formed between the two circuit boards. The two circuit boards may be at the opposite edges of the gamma ray detector.

A housing may enclose the gap and connect with the gamma ray detector and the at least one circuit board. A heat exchanger and/or fan may connect with the housing. The heat exchanger may be positioned along the first surface of the gamma ray detector.

In other embodiments, the at least one circuit board is a field programmable gate array electronically connected to an analog-to-digital converter board. The analog-to-digital converter board electronically connects with the gamma ray detector so that analog signals from the gamma ray detector are passed to the field programmable gate array as digital signals.

The gap may include some objects. In one embodiment, the gap is free of solids. The gap is bordered by the circuit boards, housing, detector, and/or other components. By including more gas or volume for the gap, less attenuation due to solids in the gap results.

In one embodiment, the gamma ray detector and the at least one circuit board form a first module. At least a second module is formed with a second gamma ray detector and at least a second circuit board forming a second gap in the second module. The first module stacks with the second module, forming a polyhedron. For example, the gamma ray detector of the first module may be parallel and opposite the gamma ray detector of the second module. The at least one circuit board of the first module forms a side wall extending between the gamma ray detectors of the first and second modules, and the gap of the first module is between the gamma ray detectors of the first and second modules. This example may be used to for a Compton camera. The gamma ray detector of the first module is configured as a scatter detector of a Compton camera, and the gamma ray detector of the second module is configured as a catcher detector of the Compton camera.

As another example, the first module is positioned adjacent to the second module so that the gamma ray detectors of the first and second modules are not in a same plane. For example, the gamma ray detector of the first module is positioned so that the first surface of the gamma ray detector of the first module is 45-135 degrees to the first surface of the gamma ray detector of the second module.

The gamma ray detector system, such as one module or multiple modules, may be used in various applications. For example, the gamma ray detector is a detector of a medical nuclear imaging system.

In a second aspect, a Compton camera is provided for medical imaging. A scatter module has a scatter detector and first electronics. The first electronics are positioned at about 90 degrees to the scatter detector to form a side wall extending from the scatter detector. A catcher module has a catcher detector and second electronics. The second electronics are positioned at about 90 degrees to the catcher detector to form a side wall extending from the catcher detector. The scatter module is stackable with the catcher module such that at least the side wall of the scatter module and/or the catcher module separate and create a space between the scatter detector from the catcher detector.

In one embodiment, the first electronics are two circuit boards extending from opposite edges of the scatter detector to form opposite side walls, and the second electronics comprise two circuit boards extending from opposite edges of the catcher detector to form opposite side walls. The space when stacked includes four side walls from the opposite side walls of the scatter module and the opposite side walls of the catcher module.

In a third aspect, a method is provided for forming a gamma ray detector system. Modules are stacked together. The modules each have a gamma ray detector. The modules are stacked so that the gamma ray detectors of the modules are in different planes. The stacked modules are electrically connected.

In one embodiment, the modules are stacked with an air gap between the modules. The gamma ray detectors of the modules are substantially parallel where at least one side wall of the air gap is formed by a circuit board having a signal processor.

In another embodiment, the modules are stacked so that the gamma ray detectors of the modules are substantially perpendicular to each other. In yet another embodiment, each gamma ray detector is a slab having opposite largest surfaces parallel to each other. The opposite largest surfaces of the gamma ray detectors of the different modules are stacked to be in the different planes.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A 3D tileable gamma ray detector is provided. Modules are used for tiling. In a module, the readout electronics are in adjoining spaces relative to the sensor plane. This positioning keeps active and inactive areas in optimal geometry to minimize photon attenuation and maximize the signal-to-noise ratio (SNR) in preferred directions. The modularity allows for flexible design geometry optimized to individual requirements and ease of maintenance.

The 3D tileable gamma ray detectors may be used in various applications, such as a Compton camera. Other applications include medical imaging applications that require electronic collimation, calorimeters, space telescopes, compact imaging systems, or other radiation detection applications.

Figure 1:
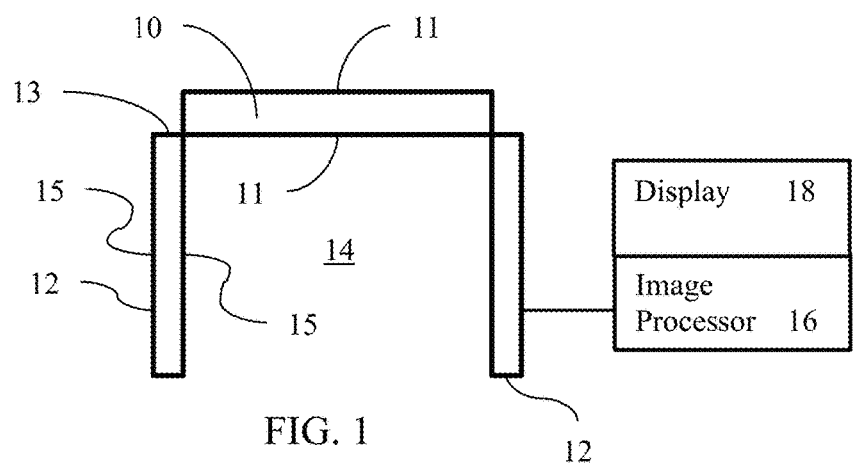
FIG. 1 is a cross-section view, according to one embodiment, of a gamma ray detector with sidewalls formed by circuit boards.

FIG. 1 shows one embodiment of a gamma ray detector system, such as for medical imaging. For example, the gamma ray detector system is for medical nuclear imaging system, such as a single photon emission computed tomography (SPECT), positron emission tomography (PET), or Compton medical imaging system.

The gamma ray detector system includes a detector 10 and circuit boards 12 forming a gap 14 (shown in cross-section), an image processor 16, and a display 18. Additional, different or fewer components may be provided. For example, the display 18 and/or image processor 16 are not provided. As another example, additional detectors 10 and/or imaging system components (e.g., a bed, housing, power source, and/or gantry) are provided.

The gamma ray detector 10 is a solid-state detector. Any material may be used, such as Si, CZT, CdTe, HPGe, and/or other material. The detector 10 is created with wafer fabrication at any thickness, such as about 4-10 mm or 1-25 mm for CZT.

The detector 10 is formed as a wafer, such as having a plate or slab shape. The detector 10 may be an array of sensors, placed side-by-side, rather than a single sensor. A minimum gap minimizing any efficiency losses may be provided so that the array behaves like a continuous wafer. The plate has two parallel, largest surfaces 11 and any thickness between the surfaces 11, such as 4 mm for CZT. The plate and corresponding surfaces 11 may have any shape, such as 5×5 cm square, rectangular, hexagon, or other polygon shape. The shape may be of various geometries, such as polyhedron (pyramid or trapezoidal). In alternative embodiments, the surfaces 11 are not parallel, such as forming a wedge shape in cross-section. Non-plate structures may be used, such as cuboid or polyhedron shapes. Any size area and/or thickness may be provided.

The detector 10 forms an array of sensors. For example, the 5×5 cm detector 10 is a 21×21 pixel array with a pixel pitch of about 2.2 mm. Other numbers of pixels, pixel pitch, and/or size of arrays may be used.

The detector 10 may include semiconductor formatted for processing. For example, the detector 10 includes an application specific integrated circuit (ASIC) for sensing photon interaction with an electron in the detector 10 and/or for analog-to-digital conversion (ADC) of signals for detected emissions. The sensed signal may be conditioned, such as amplified, and sent to one or more of the circuit boards 12. A flexible circuit, wires, or other communications path carries the signals from the ASIC to the circuit board 12.

The ASIC is collocated with the pixels of the detector 10. The ASIC is of any thickness. A plurality of ASICs may be provided, such as 9 ASICS in a 3×3 grid of the detector 10. In other embodiments, the ADC and/or processors for sensing functions are positioned on the circuit boards 12, in a board parallel and against the detector 10, or another location.

The circuit boards 12 are printed circuit boards, but other electronics substrates, wafers, and/or or other materials may be used. The circuit boards 12 include electronics, such as a field programmable gate array or arrays. A digital signal processor, general processor, analog circuit, digital circuit, combinations thereof, and/or other electronics components may be provided. The circuit boards 12 include traces for routing signals. The circuit boards 12 include acquisition electronics, which process the detected signals to provide parameters to the image processor 16. Any parameterization of the detected signals may be used. In one embodiment, the energy, arrival time, and position are output. Other acquisition processing may be provided, such as pairing of events and/or angle determination.

One or more connectors for physical and/or electrical connection with the detector 10, the image processor 16, the ASIC of the detector 10, and/or other electronics may be provided. For example, flexible circuit material with traces or wires connect a field programmable gate array on the circuit board 12 with an ADC board and ADC positioned along and behind or integrated into the detector 10. The ADC board electronically connects with or in the detector 10 so that analog signals from the gamma ray detector 10 are passed to the field programmable gate array of the circuit board 12 as digital signals. The connection may pass analog signals in alternative embodiments. The circuit boards 12 may connect to each other and/or other electronics, such as connecting through a galvanic connection, to a data bridge, and/or to a fiber optic data link. The fiber data link may provide the acquisition parameters for events detected by the detector 10 to the image processor 16.

Any number of circuit boards 12 for each module may be used. Two circuit boards 12 are shown. One, three four, or more circuit boards 12 may be used.

The circuit boards 12 have a plate or slab shape. The plate has two parallel, largest surfaces 15 and any thickness between the surfaces 15, such as 2-5 mm. Four edges 13 form surfaces connecting and/or between the largest surfaces 15. The plate may have any shape, such as 5×5 cm square or rectangular shape. In alternative embodiments, the surfaces 15 are not parallel, such as forming a wedge shape in cross-section. Non-plate structures may be used, such as cuboid or polyhedron shapes. Any size area and/or thickness may be provided.

One of the edges 13 of each circuit board 12 is positioned adjacent to one of the largest surfaces 11 of the gamma ray detector 10. There may be intervening connections, such as flexible circuit material, an ADC board, and/or a physical hinge, while still being adjacent. The edge 13 may directly abut the surface 11 to be adjacent. The edge 13 may be positioned along side an edge of the gamma ray detector 10 to be adjacent to the surface. In one embodiment shown in FIG. 1, the edge 13 is positioned to avoid being behind or on the surface 11 while still being adjacent. In alternative embodiments, the edge 13 is positioned behind or on the surface 11, such as within 10% of a length of the surface 11 to an edge of the surface. Where more than one circuit board 12 is provided, the edges 13 are positioned within 10% of a length of the surface 11 to different (e.g., opposite as shown in FIG. 1) edges of the surface 11 of the gamma ray detector 10.

The edge 13 is positioned adjacent to the surface 11 of the gamma ray detector 10 such that the surface 15 of the circuit board 12 is at an angle between 45-135 degrees from the surface 11 of the gamma ray detector 10. In the embodiment shown in FIG. 1, the circuit boards 12 are at about 90 degrees (perpendicular or orthogonal) to the detector 10. "About" is used to account for manufacturing tolerance and/or flexibility due to materials and stress. The two circuit boards 12 are parallel (i.e., are at a same angle to the surface 11) but may be positioned at different angles to the detector 10 (i.e., not parallel). Where the circuit boards 12 are not on opposite sides of the surface 11, the circuit boards 12 may be at the same angle (e.g., 90 degrees) to the surface 11 but not be parallel.

The relative position of the circuit boards 12 to the detector 10 forms a gap 14. The gap 14 is not enclosed but may be. Where one circuit board 12 is provided, the gap 14 is formed between the detector 10 and the circuit board 12, such as a triangular region, a trapezoidal region or a rectangular area in cross-section. The gap 14 may be a cuboid or polyhedron volume where the circuit board 12 and detector 10 form two sides. With two or more circuit boards 12, a cuboid or polyhedron volume is formed as the gap 14 with the two or more circuit boards 12 forming different side walls and the detector 10 forming yet another side wall. The relative positioning (e.g., edge 13 position and angle) of one or more circuit boards 12 and detector 10 forms the gap 14.

The gap 14 is filled with gas. For example, the gap 14 is filled with air. Other gases may be used, such as where the gap 14 is lined to form an enclosed chamber. Low gamma attenuation solids may fill the gap 14. In one embodiment, the gap 14 is free of solids. Gamma ray attenuating solids are avoided within the gap 14. Some solids, such as along edges of the gap 14 may be provided. For example, an ADC board is positioned along the surface 11 in the gap 14 for operating with the detector 10. The remainder of the gap 14 does not include solids other than support structure or electronics extending from the circuit boards 12. In one embodiment, the gap 14 is defined by the surrounding or forming structures or solids without any solids within the gap 14.

The gap 14 has any volume. The depth of the gap 14 from the detector 10 may be any depth, such as at least 10 times the thickness of the detector 10 (e.g., 40-100 mm or 1-25 mm). The depth may be a full length, more, or less of the circuit boards 12. In one embodiment, the gap volume is at least 5, 10, or 20 times a volume of the gamma ray detector 10.

The gap 14 forms a region with an area parallel to the detector 10 at least 50, 75, 90, 95, 99, or 100% of the area of the surface 11 of the detector 10. This gas filled region or volume minimizes attenuation of gamma radiation passing through the detector 10, assuming an angle that does not scatter on the side walls.

Figure 2:
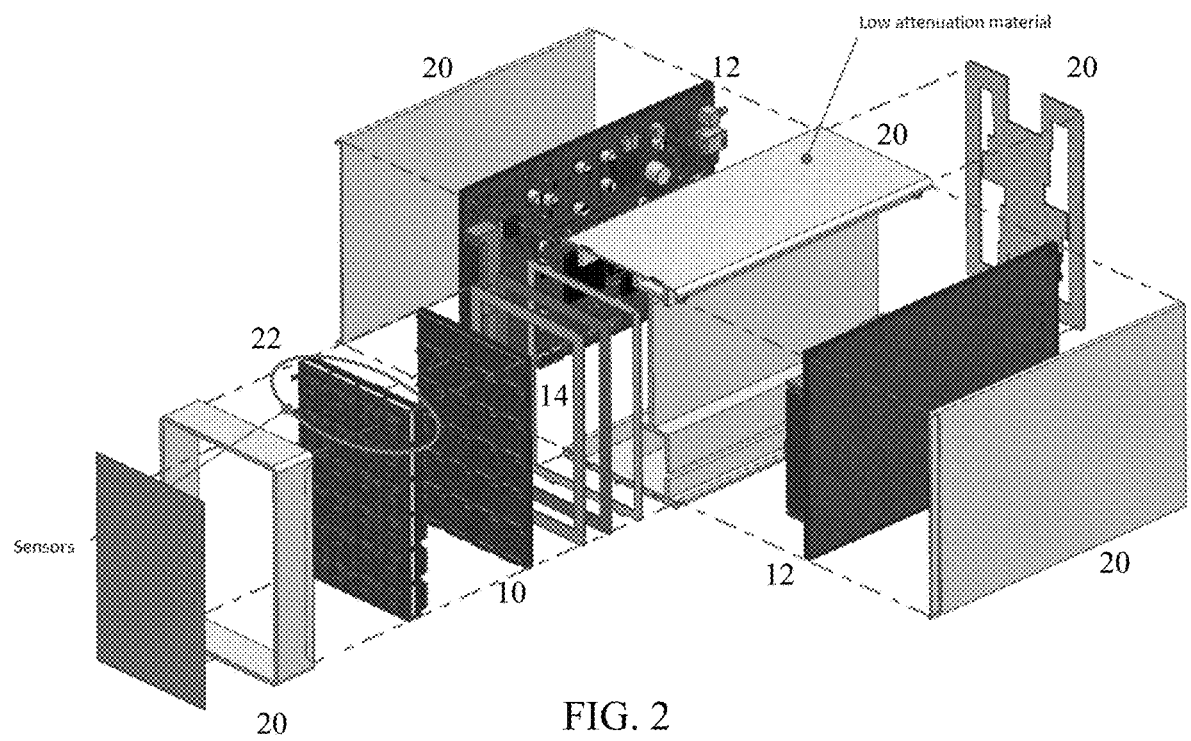
FIG. 2 is an exploded view of a 3D tileable gamma ray detector module.

FIG. 2 shows an exploded view of one embodiment of a module formed by the detector 10, a high-voltage distribution layer 22, circuit boards 12, and gap 14. The module includes a housing 20. Additional, different, or fewer components may be provided.

The housing 20 encloses at least part of the gap 14 and provides a frame to hold the detector 10 and circuit boards 12. The housing 20 may be formed from low attenuation material. The housing 20 may surround the gap 14 or may only enclose a portion of the gap 14, such as leaving one side without side walls or open. The housing 20 physically connects with the gamma ray detector 10 and/or the circuit board 12. The connection may be direct or indirect (e.g., through one or more other structures). When assembled, a generally cuboid shape is provided with the detector 10 and circuit board 12 arrangement of FIG. 1. Other than some fans and the controller and communications board, the side of the module opposite the detector 10 is open or enclosed (e.g., by fans or a frame. In other embodiments, the housing 20 may cover the opening.

The module formed by the housing 20 is shaped for being stacked, such as having flat sides. Non-flat portions, such as for air intake, may be provided. Mating structures, such as grooves, tongues, male connectors, female connectors, latches, clips, bolt and bolt holes, and/or another linkage, may be provided on the housing 20. The modules stack and/or mate with each other. In other embodiments, the housing 20 is formed to attach to a gantry or other framework with or without direct connection to any adjacent modules.

The connection or connections to the other modules or gantry may be releasable. The module is connected and may be disconnected. The connection may be releasable, allowing removal of one module or a group of modules without removing all modules.

The housing 20 forms a generally cuboid or another polyhedron shape. "Generally" is used to account for variation in shape (e.g., holes, ridges, vents, and/or chamfer) while still maintaining stackable surfaces. One or more variations, such as for air intake, may be provided. In the examples of FIGS. 1 and 2, the housing 20 forms a cuboid or other generally six-sided shape. Where the detector 10 is hexagonal or another shape, the polyhedron formed by the housing 20 may have 8 or more sides.

The housing 20 is metal, plastic, fiberglass, carbon (e.g., carbon fiber), another material, and/or combinations thereof. In one embodiment, different parts of the housing 20 are of different materials. For example, tin is used for the housing around the circuit boards 12. Aluminum is used to hold the detector 10. In another example, the housing 20 is of the same material, such as aluminum. Plastic may be used for some parts of the housing 20. Brackets, bolts, screws, clips, latches, and/or stand-offs are used to hold the circuit boards 12 and detector 10 in place within or as part of the housing 20.

The circuit boards 12 and detector 10 are within the housing 20 but may extend beyond the housing 20. The circuit boards 12 and/or detector 10 may form part of the housing 20, such as being side walls of the housing. The housing 20 may be grounded, acting as a ground plane for the circuit boards 12.

Figure 3:
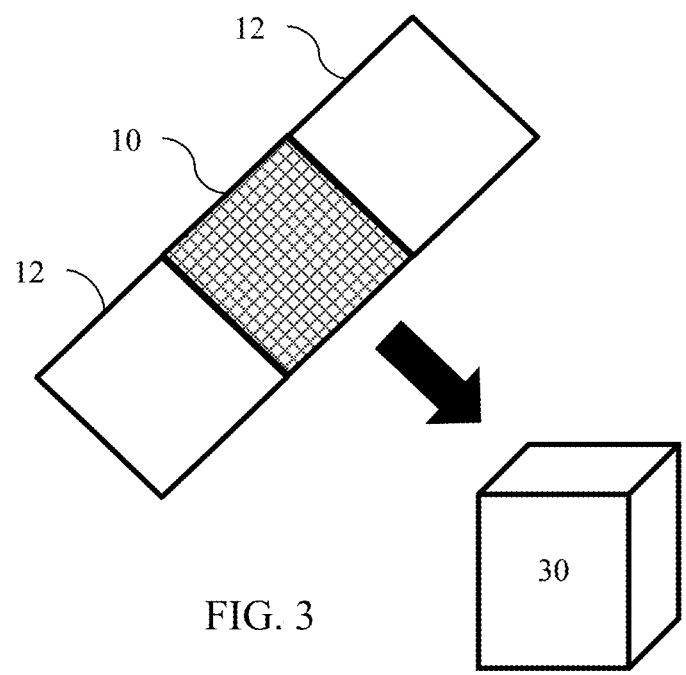
FIG. 3 illustrates formation of a cuboid gamma ray detector module.

When assembled, the detector 10 and circuit boards 12 form a module 30. FIG. 3 shows an example. The physical connection between the detector 10 and the circuit boards 12 may be flexible, such as using flexible circuit material and/or a hinge. The circuit boards 12 are then positioned at the desired angles relative to the detector 10 to form the module 30 and corresponding air gap 14. Once positioned, the circuit boards 12 are fixed in place relative to the detector 10. A fixed connection at the desired angle may be used in alternative embodiments.

Figure 4:
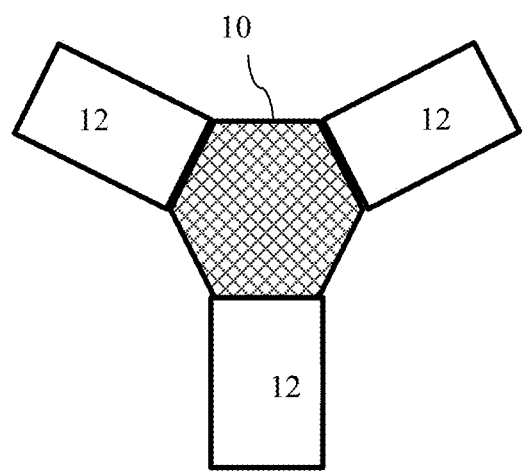
FIG. 4 illustrates formation of another embodiment of a polyhedron gamma ray detector.

FIG. 4 shows an example with a six-sided detector 10. Three circuit boards 12 connect with the detector 10. The three circuit boards 12 fold relative to the detector 10 to form the module with eight sides. Some sides may be open, such as the module 30 having three side walls formed by the circuit boards 12 and a top wall formed by the detector 10. The four remaining sides are open or formed by the housing 20. Other numbers of circuit boards 12 may be used.

The modules 30 may be stacked to form a detector array with any of various shapes. Any number of modules 30 may be stacked. Each module 30 is formed from a detector 10 and one or more circuit boards 12. A given module may include two detectors 10, such as on the top and bottom. Due to the gaps 14, a given module 30 is less likely to attenuate gamma radiation passing to the detector 10 of another module or to another detector 10, allowing stacking in 3D in addition to just 1D or 2D tiling to form one detector surface.

The stacked modules 30 may have any relative spacing and/or positioning. A gantry or frame may be used to position the modules 30 relative to each other. Alternatively, direct connection of one module 30 to another may be used to stack.

The stacking may be in 1D or 2D, such as forming a surface of detectors 10 in a same plane or curved surface. The stacking may be in 3D, such as placing the detectors 10 in different planes or outside a same curved surface. Various detection structures with detectors in two or more planes or separate surfaces may be formed.

Figure 5:
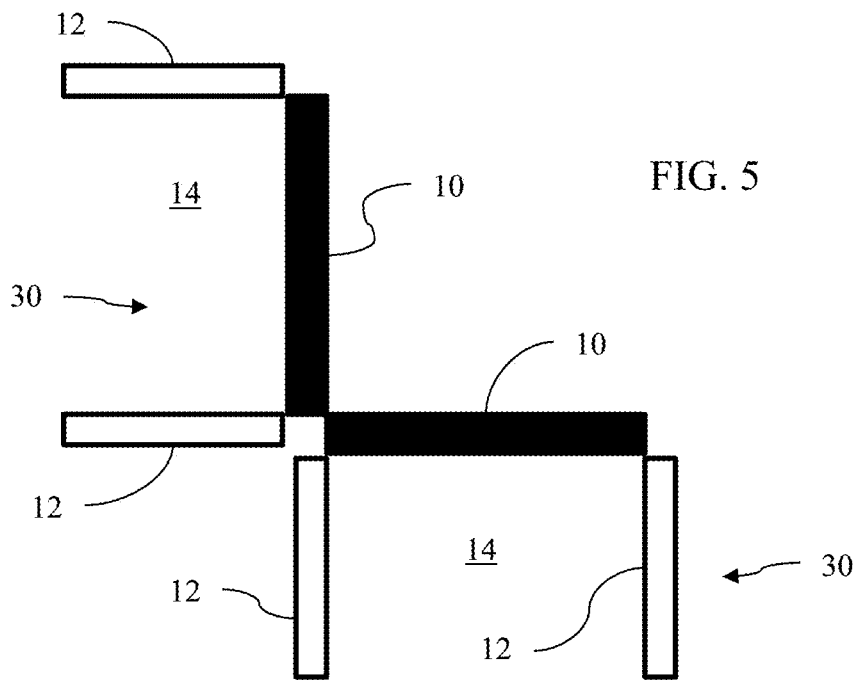
FIGS. 5 and 6 are cross-section views of two embodiments of stacking 3D tileable gammy ray detector modules.

FIG. 5 shows one example. Two modules 30 are stacked in 3D to provide detectors 10 along perpendicular planes. A third module 30 may be added to form a third plane for detection, creating a trough. Other modules 30 may be added to form an open sided cube for detection. Other modules may be added to form various shapes, such as stacking on top of each other to provide parallel detectors 10 in different planes. Complex arrangements with detectors 10 sharing one plane and other detectors 10 forming other planes or surfaces may be provided. The circuit boards 12 from different modules 30 may be placed along circuit boards or detectors and/or in gaps 14 of other modules 30. Spacing may be used to create a sparse detector of any shape. The detectors 10 may be orientated at any angle in 3D relative to each other. While FIG. 5 shows perpendicular, other angles (e.g., 5-85 or 95-175 degrees) relative to each other may be used. For example, at least two modules 30 are stacked so that the detectors form planes that are 45-135 degrees relative to each other (e.g., the surfaces 11 are 45-135 degrees from each other for two detectors 10).

Any N-gon shape may be formed. Any 3D stacking is possible, such as forming an interlocking structure, a soccer ball structure, a ring, and/or a dual or triple layer structure. The assembly or stacking may tile in 1D or 2D, extending a surface area of a detection surface formed by detectors 10 of different modules 30.

Figure 6:
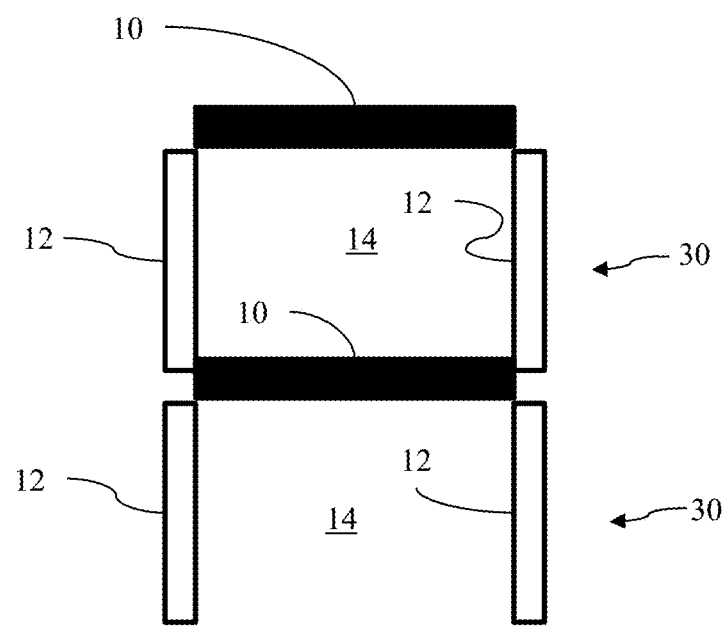

FIG. 6 shows another example stacking. One module 30 is stacked on top of another module 30, creating detectors 10 in two parallel or substantially parallel planes. "Substantially" is used to account for manufacturing tolerance and/or flexibility in materials. The stacking forms a polyhedron with six sides where one detector 10 is opposite one of the gaps 14 from the other detector 10. One or more circuit boards 12 of one module 30 form sidewalls between the detectors 10. The circuit boards 12 extend completely from one detector 10 to the other, but a gap may be provided, such as due to housing 20 or other intervening material or purposeful spacing. The gap 14 of at least one module 30 is between the two detectors 10, resulting in a low attenuation medium filling most of the space between the detectors 10.

Figure 8:
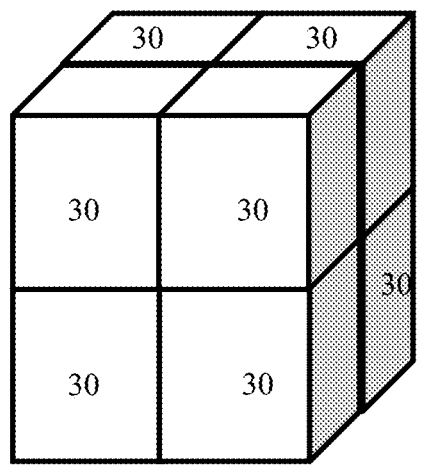
FIG. 8 is a perspective view of one embodiment of another 3D stack of gamma ray detector modules.

This stacked arrangement may include 1D or 2D tiling as well. For example, one or more modules 30 (e.g., another stack or stacks of paired modules 30) are placed adjacent to the modules 30, forming an array of modules 30. FIG. 8 shows an example with eight modules 30 tiled in 2D as a 2×2 arrangement of 3D stacked modules 30 (e.g., 2×2×2). Other stacking of more or fewer modules 30 to form cuboid, polyhedron, or other shapes may be provided. For example, a complete ring, a partial ring, a ring inside a ring, partial rings inside other partial rings, or another combination may be used. Due to the modular approach, any number of modules 30 may be used. Manufacturing is more efficient and less costly by building multiple of the same component despite use of any given module 30 in a different arrangement than used for others of the modules 30. Some modules 30 may be different than others, such as having different material and/or thicknesses of detectors 10 and/or different electronics on the circuit boards 12.

The stack of FIG. 6 may be used as a Compton camera. One detector 10, such as the upper detector in the orientation shown in FIG. 6, is used as a scatter detector. The other detector 10, such as the lower detector in the orientation shown in FIG. 6, is used as a catcher detector. For a larger area detector arrangement, the stacked modules 30 of FIG. 8 may be used. The upper detectors 10 form a 2×2 array of detectors 10 in one plane, adjacent each other. This larger scatter detector operates with the larger catcher detector formed by the 2×2 array of detectors 10 in the other plane.

Other arrangements may be used, such as forming arrays of detectors in a curved surface. One, two, three, or more layers of detectors and corresponding curved or 3D surfaces may be formed by stacking the modules 30.

Figure 7:
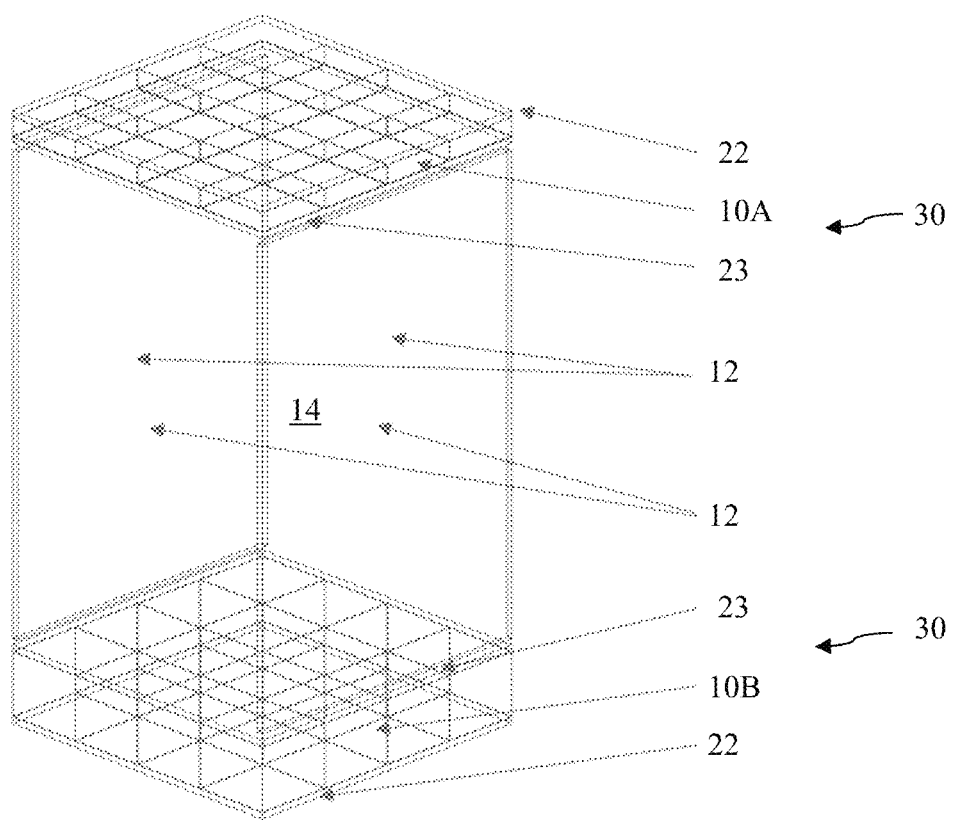
FIG. 7 is a perspective view of one embodiment of a Compton camera formed by stacking two modules.

FIG. 7 shows another stacking arrangement, such as for use as a Compton camera. Rather than the orientation shown in FIG. 6, the modules 30 are stacked so that the circuit boards 12 mate or form adjacent side walls (e.g., the lower module 30 of FIG. 6 is rotated about an axis extending out of the drawing by 180 degrees, rotated about an axis through the center of each detector 10 (10A for scatter detector and 10B for catcher detector) by 90 degrees, and slid upwards). Each module 30 has two circuit boards 12 on opposite edges of a detector 10. By rotating one module 30 relative to the other, the four side walls of circuit boards 12 are aligned to form side walls to enclose the gap 14. The result due to this nesting may use less space (e.g., not as high) than the stack of FIG. 6. A 4×4 Compton array is formed, but arrays of different sized may be used.

In FIG. 7, one module 30 includes a high-voltage distribution layer 22, detector 10A, and an ADC/ASIC board 23 to be used as part of the scatter detector. The other module 30 also includes a high-voltage distribution layer 22, detector 10B, and an ADC/ASIC board 23 to be used as part of the catcher detector. All four side walls between the scatter and catcher detectors are formed by or filled in as the circuit boards 12, two from one module 30 and two others from the other module 30.

In the example shown in FIG. 7, the detector 10 of the module 30 for the catcher detector is thicker than the detector 10 of the module 30 for the scatter detector. The scatter module 30 includes a detector 10 and electronics. The electronics are positioned at about 90 degrees to the detector 10 to form a side wall extending from the detector 10. The catcher module 30 includes a detector 10 and electronics. The electronics are positioned at about 90 degrees to the detector 10 to form a side wall extending from the catcher detector. When stacked, the electronics of both modules are on at least two side walls extending between the detectors 10. One or more sides of the stack may be open. Where four sets of electronics for a square or rectangular detector 10 are used, then all four side walls extending between the detectors 10 have electronics, two from one module 30 and two from the other module 30. The electronics of each module 30 may form opposite side walls by extending from opposite edges of the detectors 10. Alternatively, the electronics of each module 30 form two adjacent side walls.

The space or gap 14 between the detectors 10 is formed by the electronics or side walls from the different modules 30. The gap 14 is filled with gas or other low attenuation materials at energies of gamma radiation. Gamma rays may pass from (e.g., scatter or generated by collusion) or through one detector (i.e., the scatter detector) to the other detector (i.e., the catcher detector) with little attenuation in the gap 14 formed by the placement of the electronics on the side walls. The electronics create a low attenuation space due to the orientation within the modules 30.

The electronics may communicatively connect with each other even though from different modules 30. The communication may allow for event pairing. Using the energy and timing parameters, scatter and catcher events are paired. For each pair, the spatial locations and energies of the pair of events are used to find the angle of incidence of the photon on the scatter detector. Alternatively, the processing for each module 30 is performed separately, and the image processor 16 performs the pairing.

Once paired events are linked, the image processor 16 or another processor may perform computed tomography to reconstruct a distribution in two or three dimensions of the detected emissions. The angle or line of incidence for each event is used in the reconstruction. The reconstructed distribution of detected Compton events is used to render a Compton image. Where the stack is used for detection other than Compton detection, the image processor 16 may reconstruct detected emissions based on the position, energy, and/or timing information with the angle of incidence being based on physical collimation is provided on the detector 10 or detectors 10. Electronic collimation for non-Compton sensing may be provided using two layers of detectors 10.

The display 18 of FIG. 1 is a CRT, LCD, projector, printer, or other display. The display 18 is configured to display the nuclear image (e.g., a Compton image or a SPECT image). The image or images are stored in a display plane buffer and read out to the display 18. The images may be displayed separately or are combined, such as displaying the Compton image overlaid with or adjacent to the SPECT image.

Figure 9:
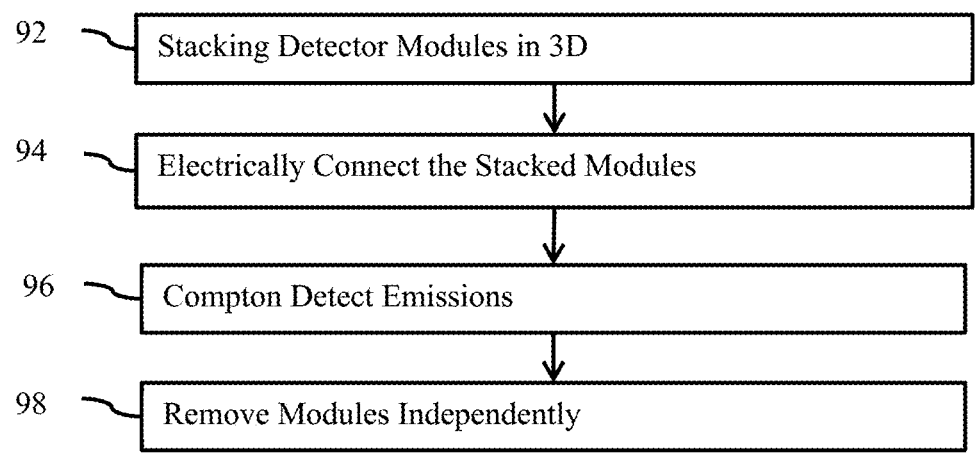
FIG. 9 is a flow chart diagram of an example embodiment of a method for forming a gamma ray detector arrangement.

FIG. 9 shows one embodiment of a flow chart of a method for forming, using, and repairing a gamma ray detector system. The gamma ray detector system is formed modularly by stacking modules in 3D. Rather than 1D or 2D tiling, 3D tiling may be used to form various detector systems, such as a Compton camera.

The method is implemented by the system of FIG. 1, the module of FIG. 2, the module of FIG. 3, the module of FIG. 4, or other modules using electronics to create a gap behind or beside the detector. The acts are performed in the order shown (i.e., top to bottom or numerically) or other orders. For example, act 98 may be performed as part of act 94.

Additional, different, or fewer acts may be provided. For example, acts 92 and 94 are provided for assembling the detector system without performing acts 96 and 98. As another example, act 96 is performed without other acts.

In act 92, two or more modules are stacked together. Each module includes a gamma ray detector. The modules are stacked or tiled in 3D so that the gamma ray detectors of the modules are in different planes (e.g., see FIGS. 5-8) and/or extended along one plane. In one embodiment, the detectors of the modules in the different planes are in substantially parallel planes. "Substantially" is used to account for tolerance and flexibility. The stacking modules have an air gap between the detectors. The air gap may be formed by having at least one side wall of the stack being formed by a circuit board with a signal processor. One or more of the modules has a circuit board extending away from the detector, so that stacking results in an air gap between detectors.

In one embodiment, each gamma ray detector of the modules being stacked is a slab having opposite largest surfaces parallel to each other. The opposite largest surfaces of the gamma ray detectors of the different modules are placed in the different planes in the stacking. In another embodiment, the modules are stacked so that the gamma ray detectors of the modules are substantially perpendicular to each other.

The modules are shaped to abut and/or mount to a gantry or frame. A person or robot places the modules relative to each other to stack in 3D. For example, a person or machine assembles a Compton sensor from two or more modules. By stacking the modules adjacent to each other with direct contact or contact through spacers, gantry, or framework, the adjacent modules form the gamma ray detector array. A full ring or a partial ring may be formed around and at least in part defines a patient or detection space.

The configuration or design of the detector system defines the number and/or position of the modules. Once stacked, the modules may be connected for communications, such as through one or more bridges, in act 94. The stacked modules are electrically connected to the image processor and/or each other through a buss, optical link, bridge, and/or another communications interface. The electronics or circuit boards of the modules may be connected with other components, such as an air-cooling system.

In act 96, the assembled detector system detects emissions. In the Compton camera example, a given emitted photon interacts with the scatter detector. The result is scattering of another photon at a particular angle from the line of incidence of the emitted photon. This secondary photon has a lesser energy. The secondary photon is detected by the catcher detector. Based on the energy and timing of both the detected scatter event and catcher event, the events are paired. Due to the air or low attenuation gap, the secondary photon is attenuated less, making it more likely to be detected. The positions and energies for the paired events provides a line between the detectors and an angle of scattering. As a result, the line of incidence of the emitted photon is determined.

In a SPECT or other gamma radiation detection example, gamma radiation is detected by one or more of the detectors. Using electronic collimation and/or physical collimation, a distribution of emissions may be reconstructed from the emissions detected by the detectors of the modules and the relative spatial positions of the modules.

The detected events are counted or collected. The lines of response or lines along which the different Compton or other emission events occur are used in reconstruction. The distribution in three dimensions of the emissions from the patient may be reconstructed. For electronic collimation, such as provided in Compton sensing, the reconstruction does not need a physical collimator as the sensing accounts for or provides the angle in incidence of the emitted photon.

The detected events are reconstructed into object space. An image may be rendered to a display device from the reconstructed events. The image represents a distribution of emissions within the patient.

In act 98, a person or machine (e.g., robot) removes one of the modules. When one of the detectors or associated electronics of a modules fails or is to be replaced (e.g., for detecting at different energies), the module may be removed. The other modules are left in the imaging system. This allows for easier repair and/or replacement without the cost of a greater disassembly and/or replacement of the entire detector system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A gamma ray detector system for medical imaging, the gamma ray detector system comprising:
   a gamma ray detector comprising a plate having first and second parallel, largest surfaces; and
   at least one circuit board having an edge between first and second parallel, largest surfaces, the edge positioned adjacent to the first surface of the gamma ray detector such that the first surface of the at least one circuit board is at an angle between 45 degrees and 135 degrees from the first surface of the gamma ray detector, a gap having gas formed between the at least one circuit board and the gamma ray detector due to the positioning of the at least one circuit board at the angle to the first surface of the gamma ray detector, the gap comprising a gap volume at least ten times a gamma ray detector volume of the gamma ray detector.

2. The gamma ray detector system of claim 1 wherein the at least one circuit board comprises two circuit boards positioned parallel to each other at the angle to the first surface of the gamma ray detector, the edges of the two circuit boards positioned within 10% of a length of the first surface to opposite edges of the first surface of the gamma ray detector such that the gap is formed between the two circuit boards.

3. The gamma ray detector system of claim 2 wherein the edges of the two circuit boards are at the opposite edges of the gamma ray detector.

4. The gamma ray detector system of claim 1 further comprising a housing enclosing the gap and connected with the gamma ray detector and the at least one circuit board.

5. The gammy ray detector system of claim 4 further comprising a heat exchanger and fan connected with the housing, the heat exchanger positioned along the first surface of the gamma ray detector.

6. The gamma ray detector system of claim 1 wherein the angle is about 90 degrees so that the at least one circuit board is about orthogonal to the first surface of the gamma ray detector.

7. The gamma ray detector system of claim 1 wherein the gas comprises air.

8. The gamma ray detector system of claim 1 wherein the at least one circuit board comprises a field programmable gate array electronically connected to an analog-to-digital converter board, the analog-to-digital converter board electronically connected with the gamma ray detector so that analog signals from the gamma ray detector are passed to the field programmable gate array as digital signals.

9. The gamma ray detector system of claim 1 wherein the gap is free of solids.

10. The gamma ray detector system of claim 1 wherein the gamma ray detector and the at least one circuit board form a first module, further comprising at least a second module formed with a second gamma ray detector and at least a second circuit board forming a second gap in the second module.

11. The gamma ray detector system of claim 10 wherein the first module stacks with the second module forming a polyhedron, the gamma ray detector of the first module parallel and opposite the gamma ray detector of the second module, the at least one circuit board of the first module forming a side wall extending between the gamma ray detectors of the first and second modules, and the gap of the first module being between the gamma ray detectors of the first and second modules.

12. The gamma ray detector system of claim 11 wherein the gamma ray detector of the first module is configured as a scatter detector of a Compton camera and the gamma ray detector of the second module is configured as a catcher detector of the Compton camera.

13. The gamma ray detector system of claim 10 wherein the first module is positioned adjacent to the second module so that the gamma ray detectors of the first and second modules are not in a same plane.

14. The gamma ray detector system of claim 13 wherein the gamma ray detector of the first module is positioned so that the first surface of the gamma ray detector of the first module is 45-135 degrees to the first surface of the gamma ray detector of the second module.

15. The gamma ray detector system of claim 1 wherein the gamma ray detector comprises a detector of a medical nuclear imaging system.

16. A Compton camera for medical imaging, the Compton camera comprising:
 a scatter module comprising a scatter detector and first electronics, the first electronics positioned at about 90 degrees to the scatter detector to form a side wall extending from the scatter detector; and
 a catcher module comprising a catcher detector and second electronics, the second electronics positioned at about 90 degrees to the catcher detector to form a side wall extending from the catcher detector;
 wherein the scatter module is stackable with the catcher module such that at least the side wall of the scatter module and/or the catcher module separate and create a space between the scatter detector from the catcher detector.

17. The Compton camera of claim 16 wherein the first electronics comprise two circuit boards extending from opposite edges of the scatter detector to form opposite side walls, wherein the second electronics comprise two circuit boards extending from opposite edges of the catcher detector to form opposite side walls, and wherein the space includes four side walls from the opposite side walls of the scatter module and the opposite side walls of the catcher module.

18. A method for forming a gamma ray detector system, the method comprising:
 stacking modules together, the modules each comprising a gamma ray detector, the modules stacked so that the gamma ray detectors of the modules are in different planes; and
 electrically connecting the stacked modules.

19. The method of claim 18 wherein stacking comprises stacking with an air gap between the modules and the gamma ray detectors of the modules being substantially parallel, at least one side wall of the air gap formed by a circuit board comprising a signal processor.

20. The method of claim 18 wherein stacking comprises stacking the modules so that the gamma ray detectors of the modules are substantially perpendicular to each other.

21. The method of claim 18 wherein each gamma ray detector comprises a slab having opposite largest surfaces parallel to each other, and wherein stacking comprises stacking with the opposite largest surfaces of the gamma ray detectors of the different modules in the different planes.

* * * * *

UNITED STATES PATENT AND TRADEMARK OFFICE
CERTIFICATE OF CORRECTION

PATENT NO. : 11,647,973 B2  
APPLICATION NO. : 17/302464  
DATED : May 16, 2023  
INVENTOR(S) : Alexander Hans Vija Page 1 of 1

It is certified that error appears in the above-identified patent and that said Letters Patent is hereby corrected as shown below:

In the Specification

In the Detailed Description Section, Column 5, Line 19, "One, three four, or…" should read "One, three, four, or…"

In the Detailed Description Section, Column 6, Line 54-55, "(e.g., by fans or a frame. In other embodiments, the house may cover the opening." should read "(e.g., by fans or a frame.) In other embodiments, the house may cover the opening."

In the Detailed Description Section, Column 11, Line 46, "… electronics of a modules fails…" should read "… electronics of a module fails…"

In the Claims

Column 12, Line 25, "The gammy ray…" should read "The gamma ray…"

Signed and Sealed this  
Eighth Day of October, 2024

Katherine Kelly Vidal  
*Director of the United States Patent and Trademark Office*